(12) United States Patent
Reydel et al.

(10) Patent No.: US 9,039,716 B2
(45) Date of Patent: May 26, 2015

(54) DISSECTING-SWATTING SURGICAL STAPLING DEVICE AND METHODS OF USE

(75) Inventors: Boris Reydel, West Caldwell, NJ (US); Yuri Berengolts, Rancho Sante Fe, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 749 days.

(21) Appl. No.: 12/459,430

(22) Filed: Jul. 1, 2009

(65) Prior Publication Data

US 2010/0179566 A1    Jul. 15, 2010

Related U.S. Application Data

(60) Provisional application No. 61/133,590, filed on Jul. 1, 2008.

(51) Int. Cl.
| | | |
|---|---|---|
| A61B 17/04 | (2006.01) | |
| A61B 17/08 | (2006.01) | |
| A61B 17/122 | (2006.01) | |
| A61B 17/064 | (2006.01) | |
| A61B 17/128 | (2006.01) | |
| A61B 17/10 | (2006.01) | |
| A61B 17/068 | (2006.01) | |

(52) U.S. Cl.
CPC ........... *A61B 17/1227* (2013.01); *A61B 17/128* (2013.01); *A61B 17/10* (2013.01); *A61B 17/083* (2013.01); *A61B 17/064* (2013.01); *A61B 17/068* (2013.01); *A61B 17/1285* (2013.01); *A61B 2017/0645* (2013.01)

(58) Field of Classification Search
CPC ............. A61B 17/0057; A61B 17/064; A61B 17/128; A61B 17/1285; A61B 17/08; A61B 17/083; A61B 17/10; A61B 17/1227
USPC ......... 606/139, 142, 143, 151, 157, 158, 213, 606/219
See application file for complete search history.

(56) References Cited

U.S. PATENT DOCUMENTS

| | | | | |
|---|---|---|---|---|
| 3,527,223 | A * | 9/1970 | Melvin ......................... | 606/188 |
| 3,874,388 | A * | 4/1975 | King et al. .................... | 606/232 |
| 5,222,961 | A | 6/1993 | Nakao et al. | |
| 5,342,393 | A * | 8/1994 | Stack ............................ | 606/213 |
| 5,350,399 | A * | 9/1994 | Erlebacher et al. ........... | 606/213 |
| 5,690,674 | A * | 11/1997 | Diaz ............................. | 606/213 |
| 5,725,552 | A * | 3/1998 | Kotula et al. ................. | 606/213 |
| 5,782,397 | A | 7/1998 | Koukline | |
| 6,152,935 | A * | 11/2000 | Kammerer et al. .......... | 606/144 |
| 6,226,843 | B1 * | 5/2001 | Crainich ....................... | 24/545 |
| 6,273,903 | B1 * | 8/2001 | Wilk ............................. | 606/219 |
| 6,508,828 | B1 * | 1/2003 | Akerfeldt et al. ............ | 606/215 |
| 6,626,916 | B1 | 9/2003 | Yeung et al. | |
| 6,736,828 | B1 * | 5/2004 | Adams et al. ................. | 606/213 |
| 6,860,895 | B1 * | 3/2005 | Akerfeldt et al. ............ | 606/215 |
| 6,872,214 | B2 | 3/2005 | Sonnenschein et al. | |

(Continued)

FOREIGN PATENT DOCUMENTS

WO         00/07506      2/2000

*Primary Examiner* — Dianne Dornbusch
(74) *Attorney, Agent, or Firm* — Fay Kaplun & Marcin, LLP

(57) ABSTRACT

A material-fastening device and related fastener and methods for use, and more particularly, a device with segments of the fastener capable of being independently exposed from a holding mechanism and independently attached to or placed in proximity to the material.

20 Claims, 7 Drawing Sheets

(56) References Cited

U.S. PATENT DOCUMENTS

| | | |
|---|---|---|
| 6,913,607 B2 * | 7/2005 | Ainsworth et al. ............ 606/151 |
| 7,063,715 B2 | 6/2006 | Onuki et al. |
| 7,160,314 B2 * | 1/2007 | Sgro et al. ..................... 606/220 |
| 7,175,648 B2 | 2/2007 | Nakao |
| 7,341,595 B2 * | 3/2008 | Hinchliffe et al. ............ 606/151 |
| 7,422,596 B2 * | 9/2008 | Therin et al. .................. 606/232 |
| 7,582,104 B2 * | 9/2009 | Corcoran et al. .............. 606/215 |
| 7,736,377 B1 * | 6/2010 | Anson et al. .................. 606/219 |
| 7,988,690 B2 * | 8/2011 | Chanduszko et al. .......... 606/49 |
| 8,216,260 B2 * | 7/2012 | Lam et al. ..................... 606/153 |
| 2002/0198562 A1 * | 12/2002 | Akerfeldt et al. ............. 606/213 |
| 2005/0267495 A1 | 12/2005 | Ginn et al. |
| 2006/0206146 A1 * | 9/2006 | Tenerz ........................... 606/213 |
| 2006/0282118 A1 | 12/2006 | Surti |
| 2007/0073316 A1 | 3/2007 | Sgro et al. |
| 2007/0225758 A1 * | 9/2007 | Preinitz et al. ................ 606/213 |
| 2007/0239209 A1 * | 10/2007 | Fallman ......................... 606/232 |
| 2007/0282357 A1 | 12/2007 | Sloan et al. |
| 2008/0243182 A1 * | 10/2008 | Bates et al. .................... 606/213 |

* cited by examiner

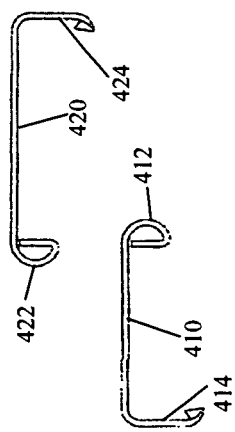
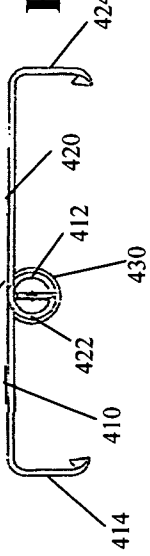
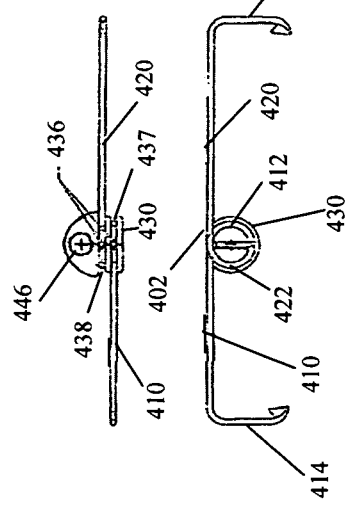
FIG. 4
FIG. 5A
FIG. 5B

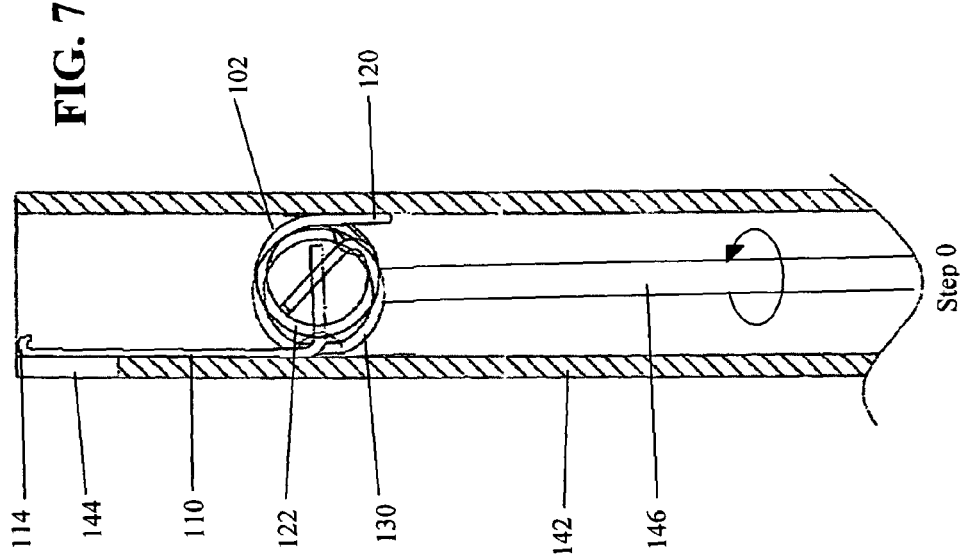

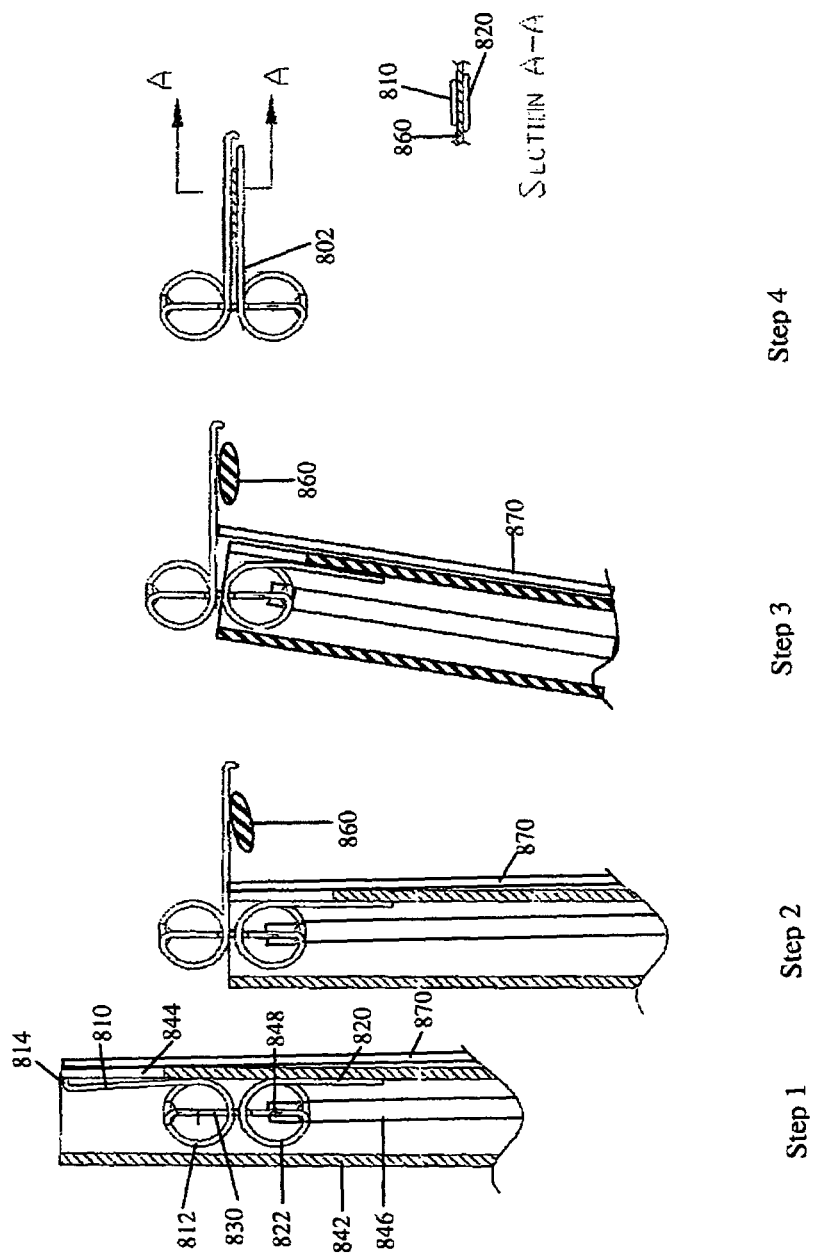

DISSECTING-SWATTING SURGICAL STAPLING DEVICE AND METHODS OF USE

This application claims the benefit of U.S. Provisional Application No. 61/133,590, filed Jul. 1, 2008, the contents of which are hereby incorporated by reference.

BACKGROUND OF THE INVENTION (1) Field of the Invention

This invention relates to a material-fastening, clamping, or stapling device and related fasteners and methods for use, and more particularly, a dissecting-swatting surgical stapling or clamping device which allows segments of the fastener to be independently attached to or placed in proximity to tissue.

(2) Description of Related Art

Fastening devices have been created in which a staple or other fastening device stored in a tubular member is pushed from the remote end of the tubular member to fasten to material, in particular tissue. U.S. Pat. No. 7,175,648 to Nakao; U.S. Pat. No. 5,222,961 to Nakao et al.; U.S. Pat. No. 7,063,715 to Onuki et al.; U.S. Pat. No. 6,872,214 to Sonnenschein et al.; U.S. Pat. No. 5,782,397 to Koukline; and U.S. Pat. No. 6,626,916 to Yeung et al.

However, these devices simultaneously expose, and simultaneously fasten tissue with, two opposite segments of the fastener. This does not allow for separate exposure and fastening with each of the two opposite segments. As a result, a sole tissue-embedded segment or a sole segment in contact with tissue may not be used to reposition the tissue in preparation for embedding or final placement of the other segment. Moreover, the first segment may not be used as a guide to make sure the fastener will become attached to the tissue in the correct position. Additionally, these devices do not provide for the device to be used with a variety of fasteners, which expose a first segment at any of a variety of angles relative to other parts of the device, and which move a second segment in any of a variety of paths to complete the fastening process.

Therefore, a need exists for an improved material-fastening, clamping, or stapling device and related fasteners and methods for use, and more particularly, a dissecting-swatting surgical stapling device and methods for use, for clamping or stapling or other uses, that provides for independent exposure and embedding or positioning of each of two segments of the fastener, and that provides for the use of the device with the aforementioned flexibility of segment positioning and segment movement.

SUMMARY OF THE INVENTION

The present invention relates to a material-clamping or material-swatting device, and in particular to a material-clamping or material-swatting device having: (1) a fastener having a first segment/element, a second segment/element, and a connection portion connecting the first segment to the second segment, (2) a moving mechanism/means for moving the second segment, (3) a holding mechanism/means for releasably holding the fastener, and (4) an exposing mechanism/means for exposing the first segment independently of exposing the second segment such that the first segment, when exposed by the exposing mechanism independently of the second segment, is or becomes disposed at a first angle relative to the holding mechanism/means, and for exposing the second segment, such that the second segment, when exposed, is moved by the moving mechanism such that it becomes disposed at substantially the same angle as the first segment relative to the holding mechanism.

In another embodiment of the invention, the moving mechanism, when moving the second segment such that it becomes disposed at substantially the same angle as the first segment relative to the holding mechanism, causes the second segment to travel an angular distance, or rotate, greater than zero degrees but less than one-hundred and eighty degrees.

In a different embodiment of the invention, the moving mechanism, when moving the second segment such that it becomes disposed at substantially the same angle as the first segment relative to the holding mechanism, causes the second segment to travel an angular distance greater than one-hundred and eighty degrees.

In a different embodiment of the invention, the moving mechanism, when moving the second segment such that it becomes disposed at substantially the same angle as the first segment relative to the holding mechanism, causes the second segment to travel an angular distance equal to one-hundred and eighty degrees.

In one embodiment, the first angle is less than one-hundred and eighty-degrees. In a related embodiment, the first angle is substantially equal to ninety degrees. In a different embodiment, the first angle is substantially equal to one-hundred and eighty degrees.

In a further embodiment of the invention, the moving mechanism, upon the exposing of the second segment by the exposing mechanism, automatically moves the second segment such that the second segment becomes disposed at substantially the same angle as the first segment relative to the holding mechanism. In yet another embodiment, there is a second moving mechanism/means for, upon the exposing of the first segment by the exposing mechanism, automatically moving the first segment to the first angle relative to the holding mechanism. In one embodiment, at least one of the moving mechanism and the second moving mechanism is a spring. In a further embodiment, the spring is semi-circular in shape.

In another embodiment, each of the moving mechanism and the second moving mechanism is a spring that is semi-circular in shape, and the connection portion contains a first groove and a second groove, the moving mechanism being at least partially positioned within the first groove, and the second moving mechanism being at least partially positioned within the second groove.

In yet another embodiment, the second segment and the first segment extend as continuations from the moving mechanism and the second moving mechanism, respectively.

In a different embodiment, the holding mechanism is also for automatically releasing the fastener upon the second segment becoming disposed at substantially the same angle as the first segment relative to the holding mechanism.

In a further embodiment, the holding mechanism is for releasably holding more than one fastener simultaneously.

In other embodiments, one or both of the first segment and the second segment are made from flat wire.

In another embodiment, the moving mechanism is a spring, the holding mechanism is a flexible tubular member, and the exposing mechanism is a flexible rod-like member disposed within and movable relative to the tubular member.

In yet another embodiment, the moving mechanism and second moving mechanism are springs, the holding mechanism is a flexible tubular member, and the exposing mechanism is a flexible rod-like member disposed within and movable relative to the tubular member.

In another aspect of the present invention, there is a method for using a material-clamping or material-swatting device having: (1) a fastener having a first segment, a second segment, and a connection portion connecting the first segment to the second segment, (2) a moving mechanism/means, (3) a holding mechanism/means, and (4) an exposing mechanism/means, which method involves: (1) exposing the first segment with the exposing mechanism, while leaving the second segment unexposed, such that the first segment is or becomes disposed at a first angle relative to the holding mechanism, (2) placing the first segment on one side of the material, (3) exposing the second segment with the exposing mechanism, (4) moving the second segment with the moving mechanism such that the second segment becomes disposed at substantially the same angle as the first segment relative to the holding mechanism and such that at least a portion of the material is secured between the first segment and the second segment, and (5) detaching the fastener from the holding mechanism.

In yet another aspect, there is a method for using a material-clamping or material-swatting device having: (1) a fastener having a first segment, a second segment, and a connection portion connecting the first segment to the second segment, (2) a moving mechanism/means, (3) a holding mechanism/means, and (4) an exposing mechanism/means, to bind together a first piece of material and a second piece of material having a gap between them, which method involves: (1) exposing the first segment with the exposing mechanism, while leaving the second segment unexposed, such that the first segment is or becomes disposed at a first angle relative to the holding mechanism, (2) inserting at least a portion of the first segment into the first piece of material, (3) exposing the second segment with the exposing mechanism, (4) moving the second segment with the moving mechanism such that the second segment becomes disposed at substantially the same angle as the first segment relative to the holding mechanism and such that at least a portion of the first piece of material and at least a portion of the second piece of material are compressed between the first segment and the second segment, and (5) detaching the fastener from the holding mechanism.

In another embodiment, the method further involves: after inserting at least a portion of the first segment into the first piece of material, but before exposing the second segment with the exposing mechanism, moving at least a portion of the first piece of material closer to at least a portion of the second piece of material.

In a further embodiment of either of these two aspects of the present invention, the moving the second segment with the moving mechanism occurs automatically upon the exposing the second segment with the exposing mechanism. In another embodiment, the first segment becomes disposed at the first angle relative to the holding mechanism automatically upon the exposing the first segment with the exposing mechanism.

In yet another embodiment, the material involved in these methods is human or animal tissue. In one embodiment, the first and the second piece of material are each human or animal tissue.

In a further embodiment, the at least a portion of the first piece of material and the at least a portion of the second piece of material which are compressed between the first segment and the second segment are in contact.

In one embodiment, the first angle is less than one-hundred and eighty degrees, the first angle being measured as the shortest of the clockwise and counter-clockwise angular distances from the angle of the first segment to the angle of the holding mechanism. In a related embodiment, the first angle is substantially equal to ninety degrees. In a different embodiment, the first angle is substantially equal to one-hundred and eighty degrees.

In a further embodiment, the moving mechanism, when moving the second segment such that it becomes disposed at substantially the same angle as the first segment relative to the holding mechanism, causes the second segment to travel an angular distance greater than one-hundred and eighty degrees. In another embodiment, this angular distance is one-hundred and eighty degrees, while in yet another embodiment, this distance is greater than zero degrees but less than one-hundred and eighty degrees.

In an additional embodiment, the holding mechanism simultaneously holds a plurality of fasteners, and the method is carried out at least two times using at least two of the plurality of fasteners.

In yet another embodiment, the moving mechanism is a spring, the holding mechanism is a flexible tubular member, and the exposing mechanism is a flexible rod-like member disposed within and movable relative to the tubular member.

In yet another aspect of the present invention, there is a material-clamping, material-swatting, or material-stapling device having: (1) a fastener having a first segment, a second segment, and a connection portion connecting the first segment to the second segment; (2) a first semi-circular spring configured to rotate the first segment; (3) a second semi-circular spring configured to rotate the second segment; (4) a holding mechanism/means configured to releasably hold the fastener; and (5) an exposing mechanism/means configured to expose the first segment independently of exposing the second segment such that the first segment, when exposed by the exposing mechanism independently of the second segment, is rotated by the first semi-circular spring, and configured to expose the second segment, such that the second segment, when exposed, is rotated by the second semi-circular spring. In one embodiment, the connection portion contains a first groove and a second groove, wherein the first semi-circular spring is positioned at least partially within the first groove, and wherein the second semi-circular spring is positioned at least partially within the second groove. In another embodiment, the first segment and the second segment extend as continuations from the first semi-circular spring and the second semi-circular spring, respectively. In yet another embodiment, the holding mechanism is configured to releasably hold more than one fastener simultaneously.

In another embodiment, the holding mechanism is a flexible tubular member, and the exposing mechanism is a flexible rod-like member disposed within and movable relative to the tubular member.

In another embodiment, the method is performed at least partially within a gastro-intestinal tract. In yet another embodiment, the method further comprises the step of rotating at least a portion of the fastener which has not yet been exposed. In one embodiment, the rotation occurs about an axis extending from a proximate end of the holding mechanism to a remote end of the holding mechanism.

In another embodiment of the above embodiments of methods and devices, the fastener is at least partially made of a metal, an alloy, a plastic, or a polymer. In additional embodiments, the first segment is integral with the second segment. In other embodiments, the first segment is separate from the second segment.

In another embodiment, the device further includes an angling mechanism for adjusting the angle of the first segment relative to the holding mechanism. In an additional embodiment, the method further involves the step of, after exposing the first segment, but before exposing the second segment, adjusting the angle for the first segment relative to the holding mechanism with the angling mechanism.

BRIEF DESCRIPTION OF THE DRAWINGS

FIG. 4 shows some parts of a staple-like fastener according to an embodiment of the present invention;

FIG. 5A is a top-view of a complete staple-like fastener in a relaxed position according to an embodiment of the present invention, which complete staple-like fastener includes, inter alia, the parts of FIG. 4;

FIG. 5B is a front-view of the complete staple-like fastener of FIG. 5A, with rod 446 omitted from this front-view;

FIG. 7 shows preliminary step 0 of the method of one embodiment of the present invention shown in FIG. 1, the tube-like member 142 shown as cutaway for easier viewing.

FIG. 8 shows steps 1-4 of a method of using an additional embodiment of the present invention, the tube 842 shown as a cutaway for easier viewing.

DETAILED DESCRIPTION OF THE INVENTION

Figure 1:
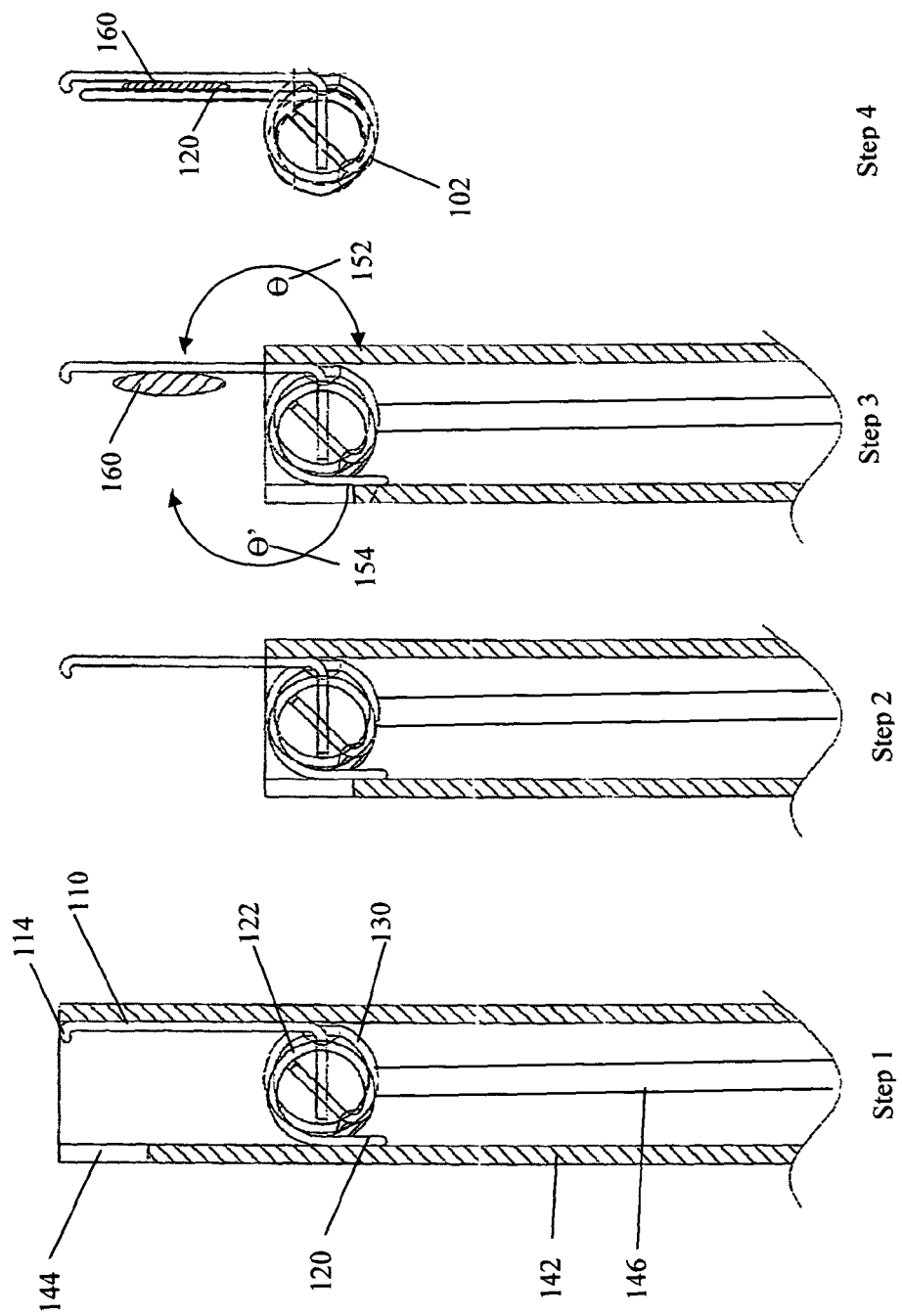
FIG. 1 shows steps 1-4 of a method of using one embodiment of the present invention, the tube-like member 142 shown as cutaway for easier viewing.
Figure 2:
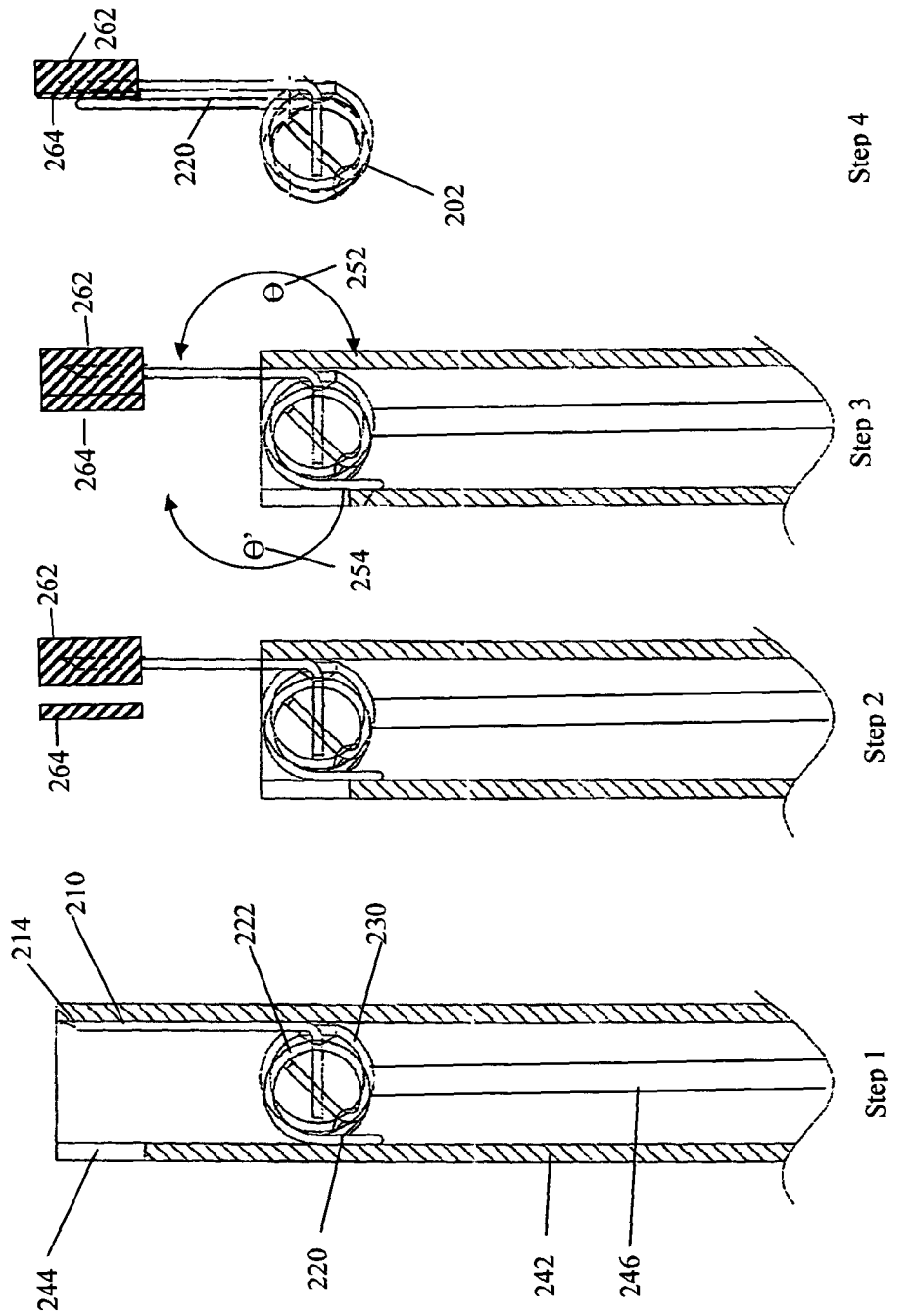
FIG. 2 shows steps 1-4 of a method of using a different embodiment of the present invention, the tube-like member shown as cutaway for easier viewing.
Figure 3:
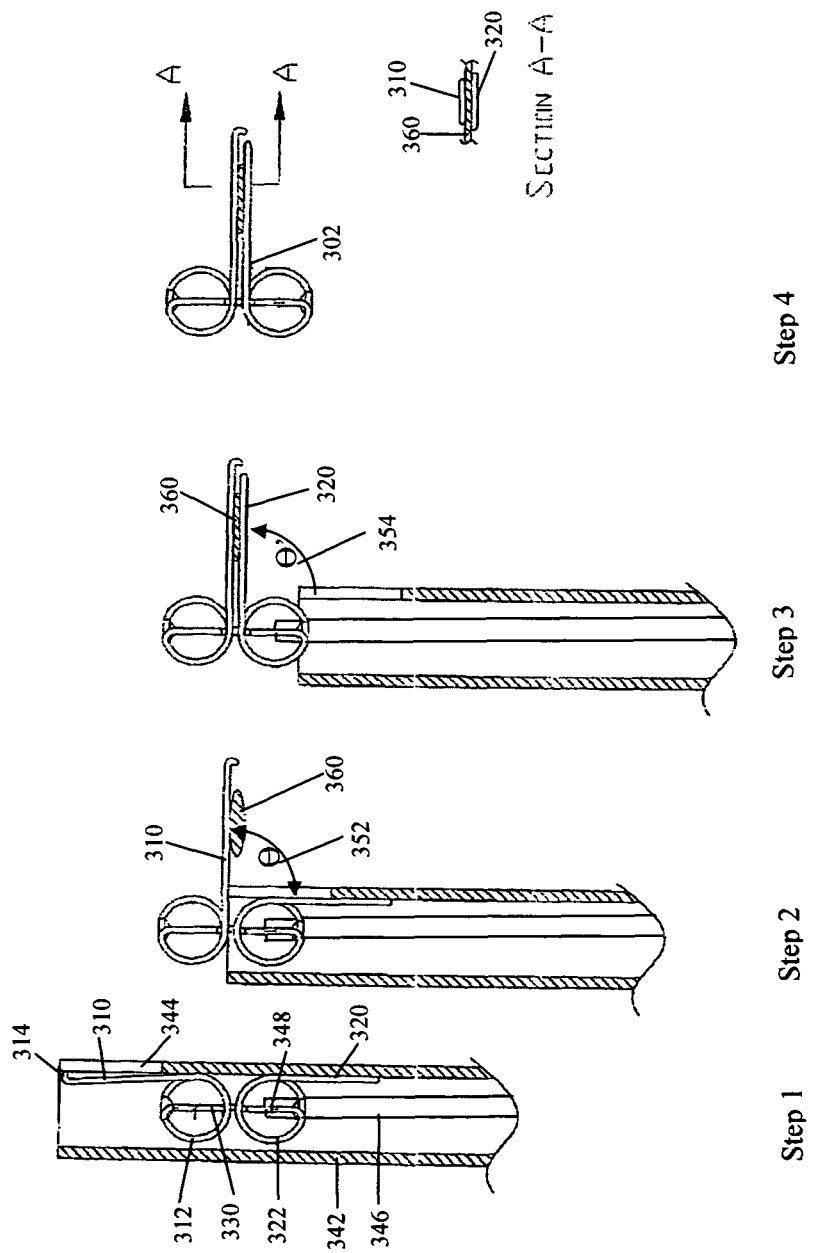
FIG. 3 shows steps 1-4 of a method of using yet another embodiment of the present invention, the tube-like member shown as cutaway for easier viewing.

The present invention relates to a material-fastening, clamping, or stapling device and related fasteners and methods for use, and more particularly, to a dissecting-swatting surgical stapling device and methods of use, and in particular to a device with segments 110; 120; 210; 220; 310; 320; 410; 420; 610; 620 of the fastener 102; 202; 302; 402; 602 capable of being independently attached to or placed in proximity to material 160; 262; 264; 360, as exemplified in FIGS. 1-3.

One embodiment of the present invention, and a method for its use, is shown in FIG. 1. A tube 142 or other extension device is elongate, flexible, and tubular, and has an outer diameter small enough for being maneuverable, and a hollow interior. The flexibility is such as to allow the tube 142 to extend along a lumen of a human or animal body, that is, the flexibility of a device such as an endoscope. The tube may be made of any appropriate material, such as a plastic. The tube 142 has a proximate end and a remote end, the remote end being the end near the top of FIG. 1, and extends between these ends. While the tube 142 is flexible, and thus in use may curve, the direction extending from the proximate end to the remote end, which travels along the tube however it may be curved, shall be referred to as "forwards," while the direction extending from the remote end to the proximate end, shall be referred to as "backwards." The proximate end is used for holding and controlling the device, or for attachment to a handle or other element which allows for holding and controlling the device. During a medical procedure in which the device is to be used on tissue inside a patient, the tube 142 may be inserted remote end first into the patient. The medical procedure may be performed such that the method is performed at least partially within a gastro-intestinal tract.

The tube 142 also contains a gap 144 in one of its side walls, which, as described below, allows for exposure of the second segment 120 without the need for as much forward movement of the fastener 102 as would otherwise be required.

The rod 146, as shown in FIG. 1, which is disposed within the tube 142, is likewise elongate, flexible, and tubular. The flexibility is again such as to allow the tube 142 to extend along a lumen of a human or animal body, that is, the flexibility of a device such as an endoscope. It may also be made of a plastic. As the rod 146 occupies only a portion of the hollow interior, it may move relative to the tube 142 by being inserted further forward or pulled backward. This forward or backward movement may occur by the direct application of force to the rod 146. However, forward or backward movement may also occur by application of force to an attachment to the rod, such as a plunger.

The fastener 102, has a first segment 110 and a second segment 120, a hook-like projection 114 which extends from the first segment 110, and a connection portion 130 connecting the first segment 110 and the second segment 120 to each other. The fastener 102, and its individual components, may be made of any appropriate non-biodegradable material, such as metals, alloys, or plastics, or biodegradable material, such as polylactic resin, polycolic resin or other polymer. In the embodiment shown in FIG. 1, the first segment 110, while inside of the tube 142, extends forward along the right wall of the tube 142, while the second segment 120 extends backward along the left wall of the tube 142. Whether a segment extends forwards or backwards, the length of backwards extension, if any, and the existence and length of a gap 144 in the tube 142, all affect the amount of forward extension of the fastener 102 necessary to expose each of the segments 110; 120. Accordingly, it is understood that the invention is not limited to the particular combinations of these factors shown in the figures, but encompasses any combination of these factors. In particular, these factors should perhaps be chosen to lessen the difference in forward extension of the fastener 102 necessary to expose the first segment 110 and second segment 120 when, for example, the user is capable of greater precision, when the need for speedy operation is great, and when the cost of an accidental exposure is slight, and perhaps to increase the difference when the opposite is true.

The connection mechanism 130 is shown in FIG. 1 as a ring-shaped object connected to both the first segment 110, and to the second segment 120, by way of its moving mechanism 122. The connection mechanism 130 of FIG. 1 also connects releasably with rod 146. However, other connection mechanisms are possible, so long as they directly or indirectly connect a first segment with a second segment. One alternate connection mechanism 430 is shown in FIGS. 5A and 5B. This alternate connection mechanism or a different alternate connection mechanism utilizing similar features is understood to be usable with any of the embodiments contemplated by this invention. Alternate connection mechanism 430 contains a first groove 437, a second groove 438, and holes 436 through which straight portions of moving mechanisms 412; 422 are inserted, holding these moving mechanisms 412; 422 in place. The first segment 410 is partly positioned within the first groove 407 via its moving mechanism 412, while the second segment 420 is partly positioned within the second groove 408 via its moving mechanism 422. Since the moving mechanisms 412; 422 shown in FIGS. 4-5B are semi-circular springs, folding unfolded segments 410; 420 stores potential energy in the moving mechanisms 412; 422, for rotating the segments 410; 420 back to their original positions when unfolded using this stored potential energy. In FIG. 1, potential energy is likewise stored in the moving mechanism 122 of the second segment 120.

It is understood from the above and the figures that, through the use of a connection mechanism 130; 230; 330; 430, different orientations of segments 110; 120; 210; 220; 310; 320;

410; 420, and different degrees of folding of the segments, the device may be configured to position the segments at any angle relative to the rod 146; 246; 346 and tube 142; 242; 342, once the segments are exposed and thereby no longer prevented by the side walls of the tube 142; 242; 342 from moving. Likewise, it will be understood that the segments may be configured to move to these angular positions through clockwise rotation, or through complementary counter-clockwise rotation. In FIG. 1, for example, the first segment 110 is shown as undergoing no rotation after exposure and being positioned at an angle 152 of one-hundred and eighty degrees relative to the tube 142, while the second segment 120 is shown as rotating clockwise a total angular distance 154 of one-hundred and eighty degrees, to the same angular position as the first segment 110 relative to the tube 142. Therefore, it is understood that, depending upon the starting configuration, in arriving at substantially the same angle as the first segment 110 relative to the holding tube 142, the second segment 120 may rotate, clockwise or counter-clockwise, any number of degrees, non-limiting examples of which being ninety degrees, one-hundred and eighty degrees, and two-hundred and seventy degrees. The actual angular distance traveled by the second segment 110 in operation depends on the existence and size of a material 160 in its path. If there is no such material 160, the second segment 120 will travel an angular distance as far as possible given the configuration. However, if there is a material 160, depending on the thickness of the material, the angular distance traveled by the second segment 120 may be lessened because of resistance provided by the material 160.

In FIG. 1, there is material 160. The fastener 102 is pushed forward by the rod 146, as shown in Step 2, exposing the first segment 110. The first segment 110 is positioned in contact with one side of material 160, as shown in Step 3. This positioning may be accomplished by handling the rod 146 or tube 142 at the proximate end. Further forward movement of the fastener exposes second segment 120, which is rotated, as discussed above, by moving mechanism 122, until it comes to rest, as shown in Step 4, compressing material 160. The fastener 102 is released from the rod 146. This can occur either manually, as by rotating the rod 146; 446, which may have been threaded into the connection mechanism 130; 430 in a screw-like manner, or automatically, as by the loss of stored potential energy within the moving mechanism 122; 222; 312; 322; 412; 422, loosening the grip of the moving mechanism on the rod 146; 246; 346. However, other methods of manual or automatic release of the rod may be used, for example, mechanical linkages including releasable links and hooks, frangible links, hooks that may be straightened under tension to slide out of engagement with the fastener, a forceps-like grasper, or any other known arrangement.

This method effectively clamps the material 160. This is medically useful when the material 160 is human or animal tissue such as a blood vessel, ligament, bile duct, ovarian tube, gaping laceration or ulcer, which may benefit a patient by being clamped in this fashion.

The hook-like projection 114 of the first segment 110 advantageously prevents the material 160 from sliding out of the fastener 102 and prevents other material from unintentionally becoming trapped between the first segment 110 and the second segment 120.

A preliminary Step 0 to the method shown in FIG. 1 is shown in FIG. 7. Step 0 of FIG. 7 shows the rod 146 and the fastener 102 being rotated from an initial position different than that of Step 1 of FIG. 1, to reach the position of Step 1 of FIG. 1. This can be accomplished, for example, by gripping the rod 146, or an attachment to the rod 146, at the proximate end, and applying torque to the rod 146 directly or through the attachment, to rotate the rod 146 and the fastener 102. This rotation is useful to position the fastener 102 to be more easily or effectively attached to the material 106. It will however be understood as within the scope of this invention that this rotation of the fastener 102 can also occur after the first segment 110 is exposed, or after the first segment is placed in proximity with the material 160.

Another embodiment of the present invention, and a method for its use, is shown in FIG. 2. The embodiment and method for its use shown in FIG. 2 are largely similar to those shown in FIG. 2. Except for the changes noted herein, the descriptions pertaining to FIG. 1 are applicable to the embodiment shown in FIG. 2, although the reference numerals for FIG. 2 are 100 higher. Instead of the hook-like projection 114 of the embodiment of the device shown in FIG. 1, the first segment 210 of the embodiment of the device shown in FIG. 2 has a sharp projection 214 which is configured to be insertable into material. FIG. 2 also shows two pieces of material 262; 264 instead of the material 160 of FIG. 1, the two pieces of material 262; 264 having a gap between them. Step 2 of FIG. 2 shows first segment 210 being exposed, and the sharp portion 214 of the first segment 210 being inserted into a first piece 262 of material.

Then, in Step 3, at least a portion of the first piece 262 of material is moved closer to at least a portion of the second piece 264 of material, and the two pieces 262; 264 of material are positioned such that they are in contact with each other. In Step 4, the second segment 220 is exposed, and as it is made to rotate by movement mechanism 222, it presses on the second piece 264 of material, such that at least a portion of the second piece 264 of material and at least a portion of the first piece 262 of material are compressed between the first segment 210 and the second segment 220 when the second segment 220 becomes disposed at substantially the same angle 252 as the first segment relative to the tube 242. "Substantially the same angle," as used within this specification, refers to a difference in angle of one of a broad range of less than or equal to twenty degrees, a preferred range of less than or equal to ten degrees, and a most preferred range of less than or equal to seven degrees. The particular range chosen corresponds to the thickness of the material which the fastener will operate upon. The difference in angle may be as little as zero degrees. In this matter, the gap is closed. This is medically useful, by way of non-limiting example, in sealing a gaping wound.

FIG. 3 shows an additional embodiment of the present invention, and a method for its use. Where not otherwise mentioned herein, the features of FIG. 3 are shown as functioning similarly to the features of FIG. 1, although the reference numerals of these similar features are 200 higher. The embodiment of FIG. 3 differs from the embodiment of FIG. 1 in that the fastener 302 is configured to deploy the first segment 310 and second segment 320 at different angles and by different rotational movement, as shown in Step 2 and Step 3. The site 348 of a connection between the rod 346 and the fastener 302 is shown in Step 1. As shown in Step 2, after exposure, the first segment 310 is configured to rotate clockwise approximately ninety degrees, arriving at an angle 352 of ninety degrees relative to the tube 342. As shown in Step 3, after exposure, the second segment 320 is configured to rotate counter-clockwise a total angular distance 354 of ninety degrees, to also arrive at an angle 352 of ninety degrees relative to the tube 342.

As shown in Step 2, after exposing and rotating the first segment 310, but before exposing and rotating the second segment 320, the first segment 310 is positioned on one side of the material 360, in particular the forward side of the material. The material 360 is then compressed between the first segment 310 and second segment 320 when the second segment is also exposed and rotated, as shown in Step 3. This method is particularly useful when the direction of insertion of the tube 342 is limited, such as in an endoscopic procedure, and the tube 342 must be inserted in a direction essentially perpendicular to the direction that the segments 310; 320 of the fastener 302 must extend.

FIG. 3 shows a Section A-A of the segments 310; 320 compressing the material 360, wherein the segments 310; 320 are shown as having significantly greater width than height. This aspect of the present invention may be beneficial at least insofar as it allows for the clamping pressure to be dispersed over a larger surface area of the material 360, providing for a more secure clamp and for less damage to the material 360. This aspect can be achieved, in any of the embodiments, by, by way of non-limiting example, forming the segments 110; 120; 210; 220; 310; 320; 410; 420; 610; 620 or at least one of the segments, from a flat wire. However, it will be understood that the segments of the present invention may also be formed from another suitable material, as discussed above, or with a different ratio of height to width.

FIG. 4 shows an embodiment of segments 410; 420 according to the present invention, with semi-circular springs 412; 422, and hooks 414; 424 extending approximately perpendicularly from the direction of extension of the segments 410; 420. FIGS. 5A and 5B show top and front views, respectively, of a fastener using the segments 410; 420 of FIG. 4, with 5A also showing a top view of the rod 446 inserted into the connection portion 430 of the fastener. As discussed above, this fastener can be used in place of the fasteners shown in other embodiments. As shown in FIG. 5B, in a resting, unfolded state, first segment 410 extends in approximately the opposite direction from first segment 420 from the connection portion 430. Accordingly, unlike the other embodiments shown, when both segments 410; 420 are exposed during use as in the other embodiments shown, the segments 410; 420 will be at different angles relative to the tube. These features allow for functionality as a stapler, where the first hook 414 may be inserted into the a first piece of the material, without interference from the unexposed second hook 424, then the second segment 420 may be exposed, and then the second hook 424 may be inserted into a second piece of the material. The first piece of material may also be moved by means of the first hook 414 after insertion, before or after exposure of the second segment 420 and the second hook 424.

Figure 6:
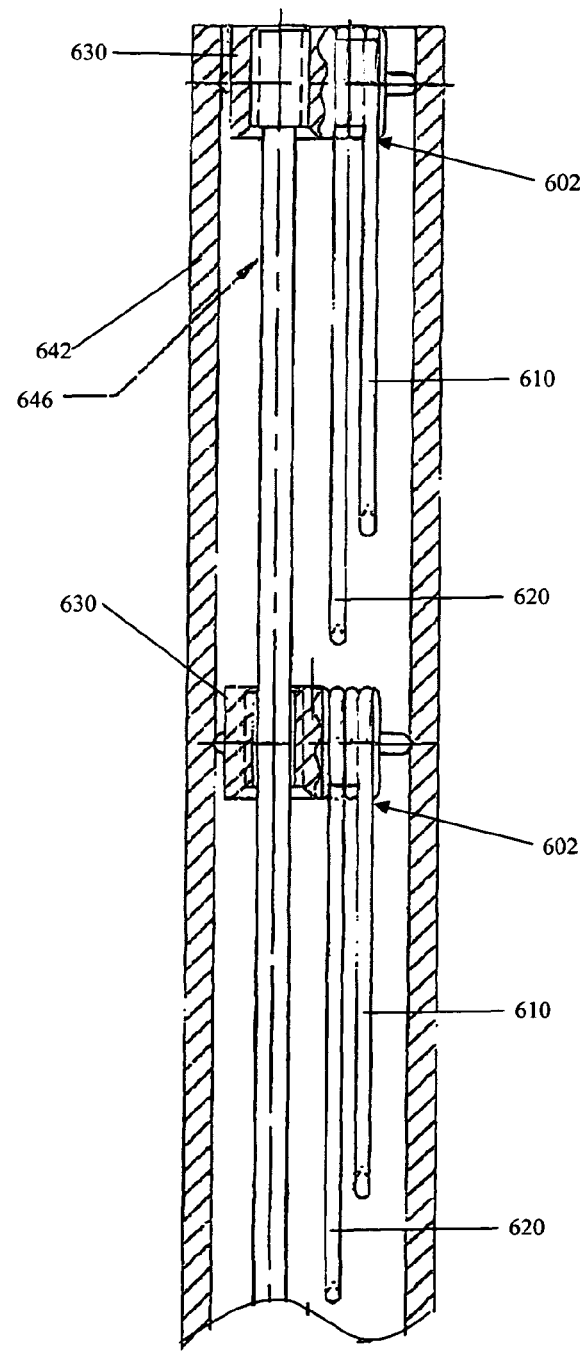
FIG. 6 is a side-view of one embodiment of the present invention, in which a plurality of fasteners are individually usable and releasable, the tube-like member shown as cutaway for easier viewing.

In yet another embodiment of the invention, shown in FIG. 6, multiple fasteners 602 are stored within the tube 642. Each is detachably connected to the rod 646 disclosed within the tube 642 by its connection portion 630. This allows for multiple fasteners 602 to be used without the need to take time to reload fasteners or, in an endoscopic medical procedure, to remove the tube 642 from the patient. The fasteners 602 may be individually detached, through the use of the devices and methods discussed in paragraph [0048] this specification.

In an additional embodiment of the invention and a method for its use, shown in FIG. 8, there is an angling mechanism/means 870 for adjusting the angle of the first segment 810 relative to the tube to any of a variety of angles. The angling mechanism may, for example, be a flexible plastic or other flexible material, on the exterior or interior of the tube 842, although other means of adjusting the angle of the first segment 810 relative to the tube 846 may be used. As shown in Step 3, this angle is adjusted by ten degrees through pressure from the angling mechanism 870, such that the first segment 810 extends in the same direction as the material 860. However, the angle may instead be adjusted by any other number of degrees, for whatever purpose necessitates this alteration. As shown in Step 4, the rod 846, the tube 842, and the angling mechanism 870, are removed from the fastener 802, the second segment 820 of which rotates to substantially the same angle as the first segment 810, causing the material 860 to be compressed between the first segment 810 and the second segment 820.

In another embodiment, a repositioning mechanism/means may reposition the fastener after the second segment has been exposed, or after the second segment has been moved by the moving mechanism. By way of non-limiting example, a device similar to, or identical to, the angling mechanism 870 may be used for this purpose.

The preceding description is presented to enable one of ordinary skill in the art to make and use the invention and to incorporate it in the context of particular applications. Various modifications, such as the use of various non-staple fasteners, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

What is claimed is:

1. A tissue treating device comprising:
   a fastener having a first element, a second element, and a connection portion connecting the first element to the second element;
   a moving mechanism having a biasing element connected to the first and second elements, the biasing element configured to move the second element relative to the first element; and
   an extension device configured to releasably hold the fastener via the biasing element, a distal end of the extension device configured to expose the first element independently of exposing the second element such that the first element is disposed at an angle relative to a longitudinal axis of the extension device when exposed, the distal end further configured to expose the second element, such that the second element, when exposed, is moved by the biasing element toward a deployed position in which, if no tissue is received between the first and second elements, the first and second elements extend from the connection portion at the angle substantially parallel to one another.

2. The device of claim 1, wherein the moving mechanism, when moving the second element such that it becomes disposed at substantially the angle relative to the holding means, causes the second element to travel an angular distance greater than zero degrees but less than one-hundred and eighty degrees from an orientation of the second element when held within the extension device.

3. The device of claim 1, wherein the moving mechanism, when moving the second element such that it becomes disposed at substantially the angle relative to the holding means, causes the second element to travel an angular distance greater than one-hundred and eighty degrees from an orientation of the second element when held within the extension device.

4. The device of claim 1, wherein the moving mechanism, when moving the second element such that it becomes disposed at substantially the angle relative to the holding means, causes the second element to travel an angular distance equal to one-hundred and eighty degrees from an orientation of the second element when held within the extension device.

5. The device of claim 1, wherein the angle is substantially equal to ninety degrees.

6. The device of claim 1, wherein the moving mechanism is configured to, upon the exposing of the second element, automatically move the second element to the angle relative to the longitudinal axis of the extension device.

7. The device of claim 6, further comprising a second moving mechanism configured to, upon the exposing of the first element, automatically move the first element to the angle relative to the longitudinal axis of the extension device.

8. The device of claim 7, wherein at least one of the moving mechanism and the second moving mechanism is a spring.

9. The device of claim 7, wherein each of the moving mechanism and the second moving mechanism is a spring that is semi-circular in shape, wherein the connection portion contains a first groove and a second groove, wherein the moving mechanism is at least partially positioned within the first groove, and wherein the second moving mechanism is at least partially positioned within the second groove.

10. The device of claim 1, wherein the extension device is configured to automatically release the fastener upon the second element becoming disposed at the angle relative to the extension device.

11. The device of claim 1, wherein the first and second elements and the connection portion are integrally formed as a unitary element.

12. The device of claim 1, wherein the first element is formed as a first member mechanically coupled to the connection portion.

13. The device of claim 12, wherein the first element is formed as a second member mechanically coupled to the connection portion.

14. A tissue gripping device comprising:
an elongate member including a holding chamber formed at a distal end thereof;
a first tissue fastener received in the holding chamber, the first tissue fastener including first and second elements coupled to one another via a connection part;
a longitudinal element extending through the elongate member to a proximal end thereof, the longitudinal element being operable to move the first tissue fastener distally from an insertion configuration to a first stage deployment position in which the first element is exposed from the holding chamber while the second element remains received therewithin and a second deployment position in which the second element of the first tissue fastener is exposed from the holding chamber; and
a first biasing arrangement biasing the first and second elements toward one another to grip tissue positioned therebetween, the first biasing arrangement operating so that, when the first element is exposed from the holding chamber and the second element is retained therein, the first element extends away from the holding chamber at a first angle relative to a longitudinal axis of the holding chamber and operating when the second element is exposed from the holding chamber so that, if no tissue is received between the first and second elements, both the first and second elements extend from the connection part at the first angle relative to the longitudinal axis of the holding chamber substantially parallel to one another, the longitudinal element being releasably coupled to the first tissue fastener via the first biasing arrangement.

15. The device of claim 14, wherein the first biasing arrangement includes a first spring connected between the first and second elements biased to rotate the first element toward a first element target position and a second spring configured to rotate the second element toward a second element target position.

16. The device of claim 15, wherein the connection portion of the first tissue fastener contains a first groove and a second groove and wherein the first spring is positioned at least partially within the first groove, and wherein the second spring is positioned at least partially within the second groove.

17. The device of claim 14, further comprising:
a second tissue fastener received in the holding chamber, the second tissue fastener including first and second elements coupled to one another via a connection part, the second tissue fastener being releasably coupled to the longitudinal element for movement distally from an insertion configuration to a first stage deployment position in which the first element thereof is exposed from the holding chamber while the second element of the second tissue fastener remains received therewithin and a second deployment position in which the second element of the second tissue fastener is exposed from the holding chamber; and
a second biasing arrangement biasing the first and second elements of the second tissue fastener toward one another to grip tissue positioned therebetween, the second biasing arrangement operating so that, when the first element of the second tissue fastener is exposed from the holding chamber and the second element is retained therein, the first element of the second tissue fastener extends away from the holding chamber at a second angle relative to a longitudinal axis of the holding chamber and operating when the second element of the second tissue fastener is exposed from the holding chamber so that, if no tissue is received between the first and second elements, both the first and second elements of the second tissue fastener extend from the connection part of the second tissue fastener at the second angle relative to the longitudinal axis of the holding chamber substantially parallel to one another.

18. The device of claim 14, wherein the first element of the first tissue fastener is integrally formed with the connection part.

19. The device of claim 14, wherein first element is formed as a separate member mechanically coupled to the connection part.

20. The device of claim 14, further comprising an angling mechanism for adjusting the first angle.

* * * * *